United States Patent
Coles et al.

[11] Patent Number: 5,873,867
[45] Date of Patent: Feb. 23, 1999

[54] ABSORBENT WITH HALF SECTION OF GELLING MATERIAL

[75] Inventors: Peter Coles, Kelkheim-Fischbach; Rainer Walter Max Schone, Koenigstein/T's; Michael Divo, Friedrichsdorf; Helene Karin Costea, Worms; Christopher Philipp Bewick-Sonntag, Kelkheim/Ts, all of Germany

[73] Assignee: The Procter & Gamble Company, Cincinnati, Ohio

[21] Appl. No.: 776,099

[22] PCT Filed: Jun. 30, 1995

[86] PCT No.: PCT/US95/08442

§ 371 Date: Jan. 10, 1997

§ 102(e) Date: Jan. 10, 1997

[87] PCT Pub. No.: WO96/01608

PCT Pub. Date: Jan. 25, 1996

[30] Foreign Application Priority Data

Jul. 12, 1994 [EP] European Pat. Off. .............. 94110800

[51] Int. Cl.⁶ .............................. A61F 13/15; A61F 13/20
[52] U.S. Cl. ......................... 604/368; 604/378; 604/381
[58] Field of Search ..................... 604/378, 368, 604/369, 372, 379, 380, 381, 382, 385.1

[56] References Cited

U.S. PATENT DOCUMENTS

| | | | |
|---|---|---|---|
| 4,381,783 | 5/1983 | Elias | 604/378 |
| 4,411,660 | 10/1983 | Dawn et al. | 604/396 |
| 4,685,915 | 8/1987 | Hasse et al. | 604/378 |
| 4,834,735 | 5/1989 | Alemany et al. | 604/368 |
| 4,935,022 | 6/1990 | Lash et al. | 604/368 |
| 4,988,344 | 1/1991 | Reising et al. | 604/380 |
| 4,994,037 | 2/1991 | Bernardin | 604/368 |
| 5,134,007 | 7/1992 | Reising et al. | 604/378 |
| 5,147,343 | 9/1992 | Kellenberger | 604/368 |
| 5,149,334 | 9/1992 | Lahrman et al. | 604/367 |
| 5,171,391 | 12/1992 | Chmielewski et al. | 604/368 |
| 5,176,668 | 1/1993 | Bernardin | 604/368 |
| 5,300,054 | 4/1994 | Feist et al. | 604/378 |
| 5,599,335 | 2/1997 | Goldman et al. | |
| 5,749,863 | 5/1998 | Payne | 604/376 |

FOREIGN PATENT DOCUMENTS

| | | |
|---|---|---|
| 0 330 675 B1 | 3/1992 | European Pat. Off. . |
| WO 91/04724 | 4/1991 | WIPO . |
| WO 91/11163 | 8/1991 | WIPO . |
| WO 91/11165 | 8/1991 | WIPO . |

*Primary Examiner*—John G. Weiss
*Assistant Examiner*—Ki Yong O
*Attorney, Agent, or Firm*—Kevin D. Hogg; Steven W. Miller; Jacobus C. Rasser

[57] ABSTRACT

An absorbent structure is described having an absorbent material layer of fibrous or foamed material, a front half section, a back half section, and absorbent gelling material, wherein more than half the weight of the absorbent gelling material is disposed in the back half section of the absorbent structure. The absorbent structure may include an acquisition/distribution layer having a surface overlying said absorbent material layer, wherein more than half of the surface is disposed in the back half section of the absorbent structure. The absorbent material layer of the absorbent structure may also have a back half section with a higher caliper than the caliper of the front half section of the absorbent material layer.

24 Claims, 7 Drawing Sheets

ABSORBENT WITH HALF SECTION OF GELLING MATERIAL

FIELD OF THE INVENTION

Absorbent structure comprising:

at least one layer of fibrous or foamed absorbent material, a perimeter comprising a front transverse edge, a back transverse edge and two longitudinal sides, a transverse center line located midway between the front transverse edge and the back transverse edge, a front half section located between the transverse center line and the front transverse edge and a back half section located between the transverse centerline and the back transverse edge, and absorbent gelling material.

The invention also relates to an absorbent article comprising such a structure.

BACKGROUND OF THE INVENTION

In the field of absorbent product technology, many attempts have been made to optimise the absorbent capacity and efficiency of absorbent cores by providing regions of increased or diminished basis weight and density in such cores.

In U.S. Pat. No. 4,935,022 (Lash) an absorbent structure is disclosed which has a lower storage layer and an upper acquisition/distribution layer comprising chemically stiffened cellulose fibers and absorbent gelling material. The upper acquisition/distribution layer is of larger surface area than the underlying storage layer. The lower storage layer is formed of an insert, which is placed relative to the upper acquisition/distribution layer such that about 75% of the absorbent gelling material in the lower layer is found in the front two-thirds section of the absorbent structure, and at least 55% of the total amount of absorbent gelling material is found in the front half section.

In U.S. Pat. No. 4,685,915 (Hasse) an absorbent product is disclosed having a core comprising hydrophilic fibers and absorbent gelling material, the core having an area of higher average density and basis weight than the end portions of the core. The area of higher average density and basis weight is located near the center or the front of the absorbent product.

In U.S. Pat. No. 4,834,735 (Alemany) an absorbent core is disclosed having a storage zone and an acquisition region of lower average density and basis weight than the storage zone. The core comprises a mixture of hydrophilic fibers and absorbent gelling particles. The acquisition region is located towards the front of the absorbent core.

In European Patent No EP-B-0 330 675, it is disclosed to introduce absorbent gelling material into specific locations of a horizontal, or x-y plane of an absorbent core using pulsed powder spray guns.

In International patent applications no's WO 91/11163 and WO 91/11165, a dual layer core is disclosed comprising a lower storage layer and an upper fluid acquisition/distribution layer comprising chemically stiffened cellulose fibers, the upper layer being substantially free of absorbent gelling material. The area of the acquisition/distribution layer is between 25% and 100% of the area of the lower storage layer, and is preferably of elongated shape. For adult incontinence products, the acquisition/distribution layer is generally located in the front two thirds of the absorbent article, relative to the backsheet.

In U.S. Pat. No. 4,411,660 (Dawn), an absorbent article is disclosed in which a layer consisting of absorbent gelling material underlies a fibrous layer. The layer of absorbent gelling material can be in the form of particles, fibers or a film.

In International patent application WO 91/04724, a diaper core is disclosed which linearly tapers from a relatively narrow crotch section to a relatively wide back section.

It has been observed by the applicant that especially in the category of adults suffering from incontinence, there is an increased tendency for leakage of the absorbent products when used in a predominantly lying-down position of the user. The majority of adults suffering from a severe incontinence are elderly women, for which leakage in this position is relatively frequent compared to other users.

It is an object of the present invention to provide an absorbent product which provides reduced leakage when used in a lying down position.

It is another object of the invention to provide an absorbent article that is especially adapted for users ranging from walking infants to adults, when confined to a predominantly lying down position.

It is a further object of the invention to provide such an absorbent article which especially reduces leakage among woman users when confined to a predominantly lying down position.

An absorbent structure according to the invention is characterised in that the weight of the absorbent gelling material located in the back half section of the structure is higher than the weight of the absorbent gelling material located in the front half section of the structure. With "back half section" of the absorbent structure is meant the part of the absorbent structure which in use is intended to contact the genitals and the buttocks of the user and extends generally towards the user's back.

Preferably between 55% and 100% by weight of the absorbent gelling material is located in the back half section. More preferably between 60% and 90% and most preferably between 65% and 80% of the absorbent gelling material is located in the back half section.

By concentrating the absorbent material in the back half section of the absorbent article, urine is prevented from leaking from the product when used in the lying down position. Hence the absorbent structures according to the invention are especially adapted to the specific needs of bedridden people.

In one embodiment of an absorbent structure according to the invention, the absorbent material may comprise, in addition to absorbent gelling material, hydrophilic fibers such as fluff pulp, rayon fibers or modified cellulosic fibers, or may be comprised of a foamed absorbent material as described in U.S. Pat. No. 5,268,224 (Desmarais). Applying more absorbent material of this kind in the back half section of the absorbent structure can result in a so-called profiled core, which is of higher caliper in the back half section than in the front half section. Alternatively, the absorbent structure may be compressed to a uniform caliper, such that the density of the structure is highest in the back half section.

In an alternative embodiment of the absorbent structure according to the invention, the total weight of the absorbent material in the back half section is increased versus the total weight of the absorbent material in the front half section. For instance, the surface area of the layer of absorbent material in the back half section may be larger than the surface area of absorbent material in the front half section at equal basis weights of absorbent material in the front half and back half sections. For instance, the distance between a longitudinal side of the absorbent structure and the longitudinal centerline may substantially monotonically increase when going from the transverse center line to the back transverse side. In this way a large surface area of absorbent material is provided in the back half section which not only provides increased absorbent capacity but also provides improved cushioning and softness to the user.

In a further embodiment of an absorbent structure according to the invention, the amount of absorbent gelling material per unit area, or average basis weight, is higher in the back half section than in the front half section.

The average basis weight of the absorbent gelling material in the front half section and in the back half section is determined by measuring the total weight of absorbent gelling material present in any one section and dividing this weight by the total area in which the absorbent gelling material is located. The weight of the absorbent gelling material is determined by separating the absorbent gelling material from the other absorbent material in any one section. The area where the absorbent gelling material is placed, is measured by applying a colouring agent to the absorbent structure, such as bromocresol. The coloured areas are detected by visual inspection. Alternatively, the absorbent structure may be exposed to x-rays to detect the quantity and location of the absorbent gelling material.

In another embodiment of an absorbent structure according to the invention, the average basis capacity in the back half section is higher than the average basis capacity in the front half section. The average basis capacity is a measure of the amount of liquid that can be absorbed per gram of absorbent material. The average basis capacity will depend on the amount and on the type of absorbent material in the front half section and the back half section. The absorbent material in any one section may comprise for instance absorbent gelling material, fibers, foam, interpartically crosslinked aggregates or any combination thereof. The average basis capacity is measured according to a test method which is based on the official method established by the German "Medizinischer Dienst der Spitzenverbände der Krankenkassen e.V." for reimbursement of incontinence absorbent products. The test method "Prüfmethode Nr. 1/93 MDS-HI Teil 1, Bestimmung der Flüssigkeitsaufnahme" is described in the detailed description of the invention, below.

In a further embodiment of an absorbent structure according to the invention, an acquisition/distribution layer overlies a lower layer of absorbent material, such that the acquisition/distribution layer is for a larger part located on top of the back half section of the lower layer. When the acquisition/distribution layer is of generally elongated shape, a larger length of this layer extends across the back half section of the underlying layer of absorbent material. When the acquisition/distribution layer is of generally circular shape, or is relatively irregularly formed, a larger surface area of the acquisition/distribution layer extends across the back half section of the underlying layer than across the front half section.

The acquisition/distribution layer comprises fibers which retain their resiliency even when wetted, such that the absorbent capacity of the acquisition/distribution-layer does not decrease upon uptake of consecutive gushes of liquid. This property is expressed by the wet-compressibility of the acquisition/distribution layer of at least 5 cm$^3$/g and a drip capacity of at least 10 g/g. Hydrophilic fibers which have this property are found among chemically stiffened cellulosic fibers as described in U.S. Pat. Nos. 4,898,642 (Moore), 4,889,597 (Bourbon), 4,889,596 (Schoggen), 5,160,789 (Barcus), 5,049,235 (Barcus) and 4,822,453 (Dean), or by hydrophilic synthetic fibers, such as polyester fibers. The acquisition-distribution layer may alternatively or additionally comprise various types of bicomponent fibers that are thermally bonded to form an open structure. Such fibers described in EP-A-0 513 148 and U.S. application Ser. No. 08/141,156.

The acquisition/distribution layer serves to rapidly take in large gushes of liquid and to quickly lead these away from the body of the wearer, the acquisition/distribution layer has a relatively low density, for instance between 0.03 and 0.13 g/cm$^3$. Liquids are only temporarily stored in the acquisition/distribution layer. The acquisition/distribution layer is drained by the underlying storage layer, such that it is rapidly emptied and ready for uptake of further gushes of liquid.

For draining of the acquisition/distribution layer, a layer of absorbent gelling particles may be located directly underneath the acquisition/distribution layer. Preferably this absorbent gelling material is of a high gel strength, such that the particles of absorbent gelling material do not deform to such an extent as to form a gelled mass which is relatively impermeable to liquid. Preferably the absorbent gelling material used directly underneath the acquisition/distribution layer has Gel Layer Permeability (GLP) value of at least $4\times10^{-7}$cm$^3$/s/g. Absorbent gelling materials of these GLP values, maintain a relatively open structure when wet and maintain good liquid transport properties in the vertical (z-direction) and the horizontal (x-y) direction even when wet.

BRIEF DESCRIPTION OF THE DRAWINGS

The invention will be explained in detail with reference to the accompanying drawings.

In the drawings.

DETAILED DESCRIPTION OF THE INVENTION

Figure 1:
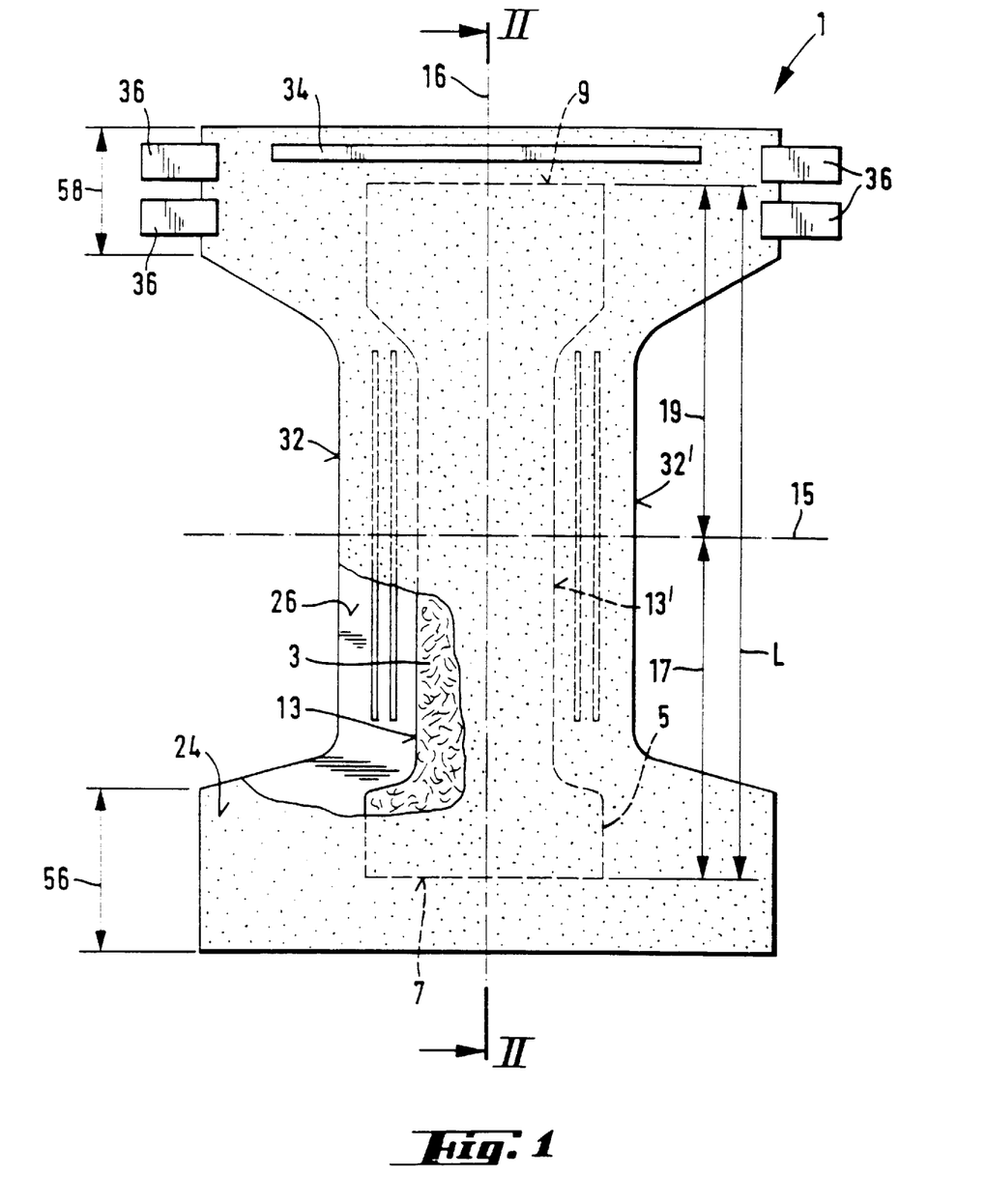
FIG. 1 shows a front elevational view of an absorbent article comprising an absorbent structure according to the invention.

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a co-ordinated entity so that they do not require separate manipulative parts like a separate holder and liner. A preferred embodiment of an absorbent article of the present invention is the unitary disposable absorbent article, or diaper as shown in FIG. 1. As used herein, the term "diaper" refers to an absorbent article generally worn by walking infants and incontinent persons that is worn about the lower torso of the wearer. It should be understood, however, that the present invention is also applicable to other absorbent articles such as incontinent briefs, incontinent undergarments, diaper holders and liners and the like.

Figure 11:
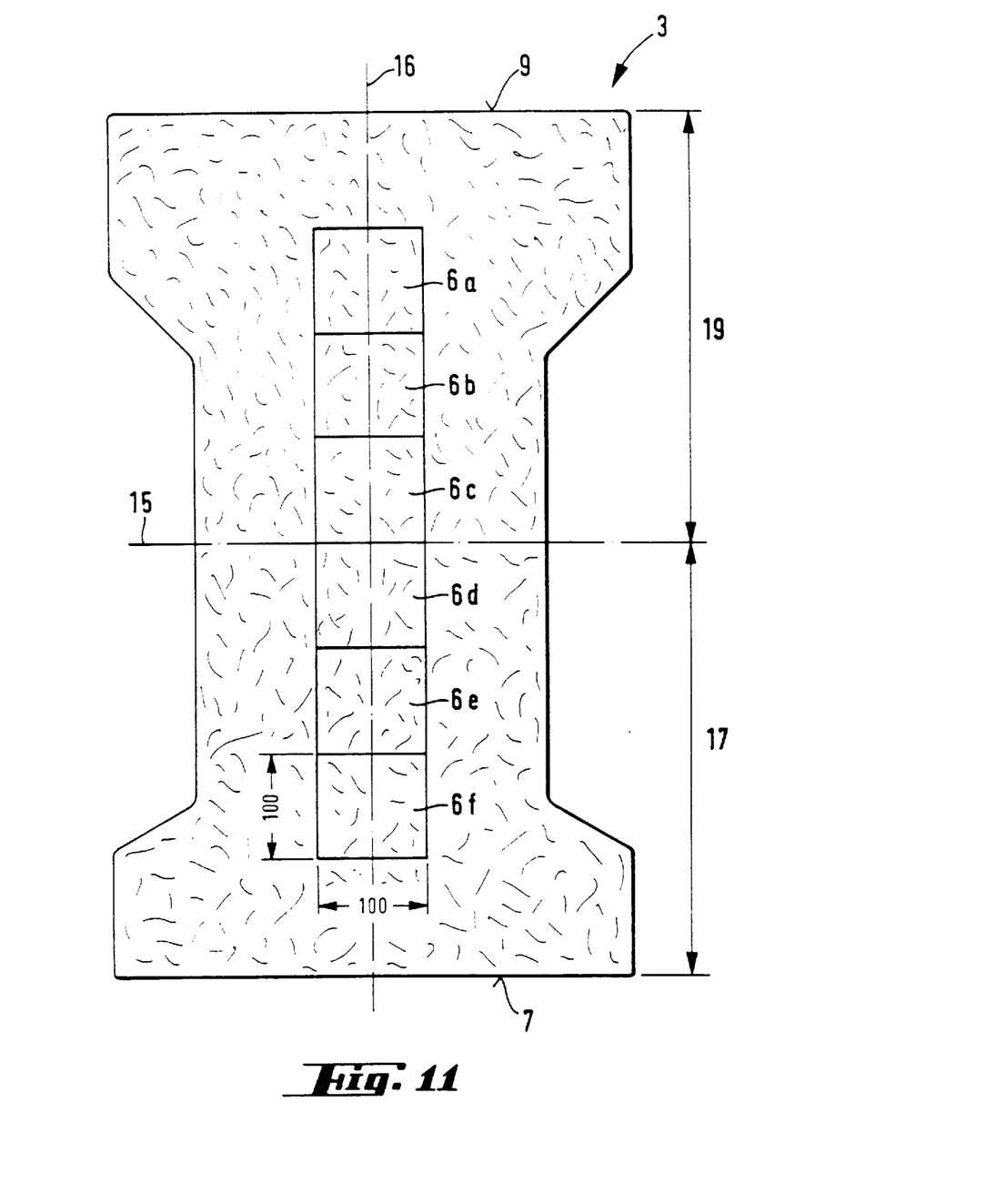

FIG. 1 shows the absorbent article 1, comprising an absorbent structure, or core 3. The absorbent core 3 comprises a perimeter 5 having a front transverse edge 7, a back transverse edge 9 and two longitudinal sides 13,13'. An imaginary transverse center line 15 is located midway between the front transverse edge 7 and the back transverse edge 9 and divides the core 3 into a front half section 17 and a back half section 19. In the absorbent core according to the invention, the amount of absorbent gelling material in the back half section 19 is larger than the amount of absorbent material in the front half section 17. Preferably, the average amount of absorbent gelling material per unit area, or average basis weight, in the back half section 19 is higher than in the front half section 17, at least in a central section 6a–6f as indicated in FIG. 11.

In FIG. 1, the absorbent article, or diaper 1 is shown in its flat-out, uncontracted state (i.e., with elastic induced contraction pulled out) with portions of the article being cutaway to more clearly show the construction of the diaper 1 and with the portion of the diaper 1 which faces or contacts the wearer, the inner surface, oriented towards the viewer. As shown in FIG. 1, the diaper 1 preferably comprises a liquid pervious topsheet 24; a liquid impervious backsheet 26 joined with the topsheet 24; the absorbent structure, or core 3 being positioned between the topsheet 24 and the backsheet 26; elasticized leg cuffs 32, 32'; an elastic waist feature 34; and a fastening system generally multiply designated as 36 and located in the back waist region 58 of the diaper.

FIG. 1 shows a preferred embodiment of the diaper 1 in which the topsheet 24 and the backsheet 26 have length and width dimensions generally larger than those of the absorbent core 3. The topsheet 24 and the backsheet 26 extend beyond the perimeter 5 of the absorbent core 3. While the topsheet 24, the backsheet 26, and the absorbent core 3 may be assembled in a variety of well known configurations, preferred diaper configurations are described generally in U.S. Pat. No. 3,860,003 entitled "Contractable Side Portions for Disposable Diaper" which issued to Kenneth B. Buell on Jan. 14, 1975; and U.S. patent application Ser. No. 07/715, 152, allowed, "Absorbent Article With Dynamic Elastic Waist Feature Having A Predisposed Resilient Flexural Hinge", Kenneth B. Buell et al. filed Jun. 13, 1991; each of which is incorporated herein by reference.

The absorbent core 3 may be any absorbent means which is generally compressible, conformable, non-irritating to the wearer's skin, and capable of absorbing and retaining liquids such as urine and other certain body exudates. The absorbent core 3 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers, tissue including tissue wraps and tissue laminates; absorbent foams; absorbent sponges; superabsorbent polymers; absorbent gelling materials; or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 3 should, however, be compatible with the design loading and the intended use of the diaper 1. In a preferred embodiment according to the invention, the absorbent core is intended for use by adults or juveniles and is able to absorb between 100 and 1000 ml of body fluids. Further, the size and absorbent capacity of the absorbent core 3 may be varied to accommodate wearers ranging from infants through adults. Exemplary absorbent structures for use as the absorbent core 3 are described in U.S. Pat. No. 4,610,678 entitled "High Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. Each of these patents are incorporated herein by reference. A preferred embodiment of the absorbent core 3 has longitudinal dimension, L, of about 60 cm, a back transverse edge 9 of about 30 cm, a front transverse edge 7 of about 30 cm and a width along the transverse center line 15 of about 20 cm.

The backsheet 26 is positioned adjacent the garment surface of the absorbent core 3 and is preferably joined thereto by attachment means (not shown) such as those well known in the art. For example, the backsheet 26 may be secured to the absorbent core 3 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola et al. on Mar. 4, 1986, more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 3 from wetting articles which contact the diaper 1 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mil) to about 0.051 mm (2.0 mils). Particularly preferred materials for the backsheet include RR821 blown films and RR5475 cast films as manufactured by Tredegar Industries, Inc. of Terre Haute, Ind. The backsheet 26 is preferably embossed and/or matte finished to provide a more clothlike appearance. Further, the backsheet 26 may permit vapors to escape from the absorbent core 3 (i.e., breathable) while still preventing exudates from passing through the backsheet 26.

The topsheet 24 is positioned adjacent the body surface of the absorbent core 3 and is preferably joined thereto and to the backsheet 26 by attachment means (not shown) such as those well known in the art. Suitable attachment means are described with respect to joining the backsheet 26 to the absorbent core 3. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet 24 and the backsheet 26 are joined directly to each other in the diaper periphery and are indirectly joined together by directly joining them to the absorbent core 3 by the attachment means (not shown).

The topsheet 24 is compliant, soft feeling, and non-irritating to the wearer's skin. Further, the topsheet 24 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 24 is made of a hydrophobic material to isolate the wearer's skin from liquids contained in the absorbent core 3. The hydrophobic material may have a hydrophilic coating. There are a number of manufacturing techniques which may be used to manufacture the topsheet 24. For example, the topsheet 24 may be a nonwoven web of fibers spunbonded, carded, wet-laid, meltblown, hydroentangled, combinations of the above, or the like. A preferred topsheet is carded and thermally bonded by means well known to those skilled in the fabrics art. A preferred topsheet comprises a web of staple length polypropylene fibers such as is manufactured by Veratec, Inc., a Division of International Paper Company, of Walpole, Mass. under the designation P-8.

The diaper 1 may also comprise elasticized leg cuffs 32,32' for providing improved containment of liquids and other body exudates. Each elasticized leg cuff 32 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 1, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff.

The diaper 1 preferably further comprises an elastic waist feature 34 that provides improved fit and containment. The elastic waist feature 34 is that portion or zone of the diaper 1 which is intended to elastically expand and contract to dynamically fit the wearer's waist. The elastic waist feature 34 at least extends longitudinally outwardly from at least one of the transverse edges of the absorbent core 3 and generally forms at least a portion of one of the waist regions 56 or 58 of the diaper 1. Disposable diapers are generally constructed so as to have two elastic waist features, one positioned in the first waist region and one positioned in the second waist region, although diapers can be constructed with a single elastic waist feature. Further, while the elastic waist feature or any of its constituent elements can comprise a separate element affixed to the diaper 1, the elastic waist feature 34 is preferably constructed as an extension of other elements of the diaper such as the backsheet 26 or the topsheet 24, preferably both the backsheet 26 and the topsheet 24.

The elasticized waistband 34 may be constructed in a number of different configurations including those described in U.S. Pat. No. 4,515,595 issued to Kievit et al. on May 7, 1985 and the above referenced U.S. patent application Ser. No. 07/715,152; each of these references being incorporated herein by reference.

The diaper 1 also comprises a fastening system 36 which forms a side closure which maintains the first waist region 56 and the second waist region 58 in an overlapping configuration such that lateral tensions are maintained around the circumference of the diaper to maintain the diaper on the wearer. Exemplary fastening systems are disclosed in U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; U.S. Pat. No. 3,848,594 entitled "Tape Fastening System for Disposable Diaper" issued to Buell on Nov. 19, 1974; U.S. Pat. No. 4,662,875 entitled "Absorbent Article" issued to Hirotsu et al. on May 5, 1987; and the hereinbefore referenced U.S. patent application Ser. No. 07/715,152; each of which is incorporated herein by reference.

Figure 2:
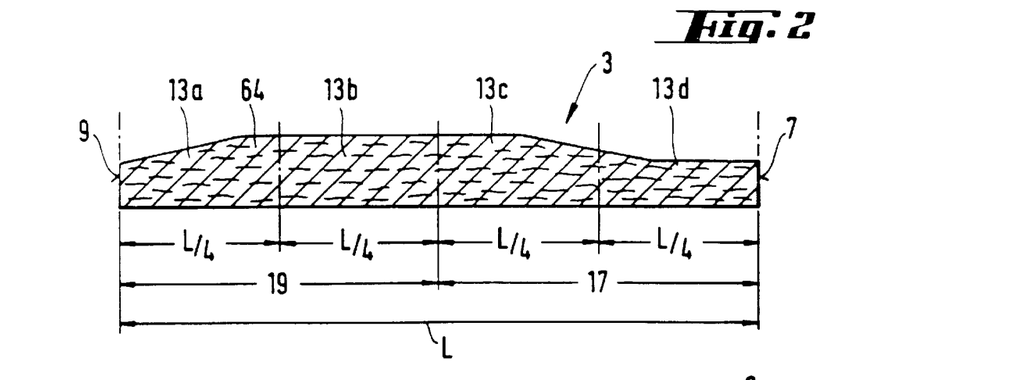
FIGS. 2 to 5 show cross-sectional views of the absorbent structure of FIG. 1 along the longitudinal center line.

FIG. 2 shows a cross-sectional view of the core 3 along the longitudinal center line 16. Within the core 3, four sections 13a,13b,13c and 13d of equal length, L/4, can be considered, the caliper of the core being different in each section. In the embodiment of FIG. 2, the core 3 comprises fluff pulp of a uniform density. The caliper of section 13a is about 7 mm. The caliper in section 13b is about 10 mm, the caliper of section 13c is about 8 mm and the caliper in section 13d is about 5 mm. Hence the ratio of the basis weights of the fibers of combined sections 13a and 13b, which form the back half section of core 3, and combined sections 13c and 13d, which form the front half section, is about 1.3.

Figure 3:
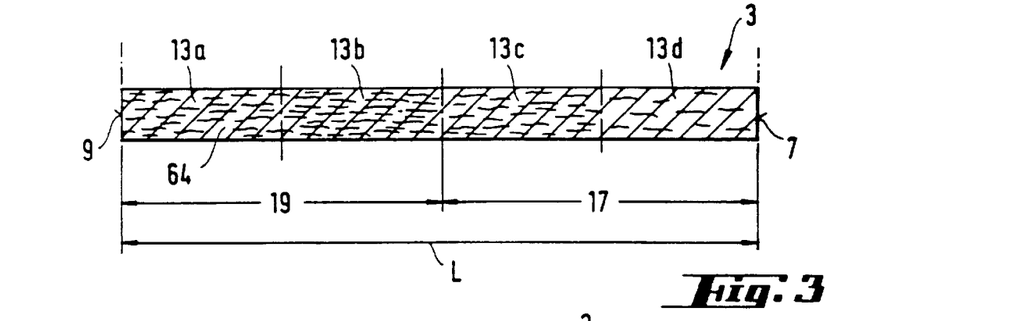

The core 3 may comprise cellulosic fibers, synthetic fibers such as crimped polyester fibers, mixtures of synthetic and cellulosic fibers or absorbent foam material as described in U.S. Pat. No. 5,268,224 (Desmarais).The caliper of the core 3 as shown if FIG. 2 can be made uniform by calendering. This is illustrated in FIG. 3. The core 3 of FIG. 3 comprises areas of relatively high density in the back half section 13a, 13b and a relatively low density in the front half section 13c,13d. The density of the fibrous or foamed absorbent material in the front and back half sections may range from 0.1 to 1 g/cm$^3$. The density in each section will be proportional to the caliper before calendering to a uniform caliper. The increased density of the fibers in the back half section improves retention of liquids in that section as the smaller interfiber capillaries will exert a higher suction on liquids in the back half section.

Figure 4:
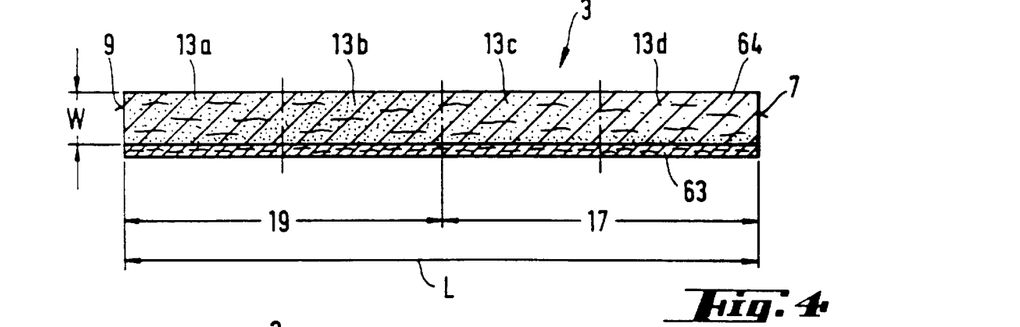

The core 3 in FIGS. 2, 3 and 4 comprises a water-insoluble, absorbent gelling material, which swells upon contact with liquids to form a hydrogel. Such materials are described in detail in U.S. Pat. No. Re. 32,649 (Brandt) and can absorb at least 20 times their own weight of liquid. The hydrogel material may be in particulate form, particle sizes ranging from 10 micrometers to 2000 micrometers or can come in the form of flakes, fibers or sheets. The hydrogel material may also be comprised of an interpartically crosslinked aggregate as described in U.S. Pat. No. 5,102, 597 (Roe). The core 3 in FIG. 4 comprises a lower layer 63, which is substantially free of absorbent gelling material or which contains small size absorbent gelling material particles or absorbent gelling material fines, as described in EP-A-0 567 738 (Plischke). The lower layer 63 serves to contain the absorbent gelling material in the upper layer 64 and to prevent the absorbent gelling material particles from contacting the backsheet and hence cause surface irregularities on the backsheet (so called "pock marking") and to prevent the absorbent gelling material from perforating the backsheet.

In the absorbent core of FIG. 4, the absorbent gelling material is uniformly dispersed through the thickness, W, of each region 13a–13d of the layer 64. However, the absorbent gelling material may be present in different concentrations throughout the thickness of layer 64 of the core 3, and may be highest in the parts of the core that are furthest away from the wearer (those parts of layer 64 that are located closest to layer 63). Such cores with a so-called absorbent gelling material "gradient" are described in detail in EP-A-0 198 683 (Duenk).

In the embodiment of FIG. 4, the basis weight of the absorbent gelling material in section 13a is about 0.012 g/cm$^2$, the basis weight in section 13b being about 0.016 g/cm$^2$, the basis weight in section 13c being about 0.012 g/cm$^2$ and the basis weight in section 13d being about 0.008 g/cm$^2$ In a preferred embodiment, section 13a contains about 25%, and section 13b contains about 35% by weight of the total amount of absorbent gelling material present in the layer 64. Section 13c may contain about 25% and section 13d about 5% of the total weight of absorbent gelling material in layer 64.

Preferably, the absorbent gelling materials are "high gel strength" materials. High gel strength absorbent gelling material particles will undergo relatively little deformation upon being wetted such that the gelling material does not flow into the capillary void space of the fibrous material and causes undesired gel blocking. Suitable absorbent gelling materials have Gel Layer Permeability (GLP) values higher than 4×10$^{-7}$ cm$^3$/s/g. The GLP value can be measured by the method as described in European Application No. 93309614.1.

Figure 5:
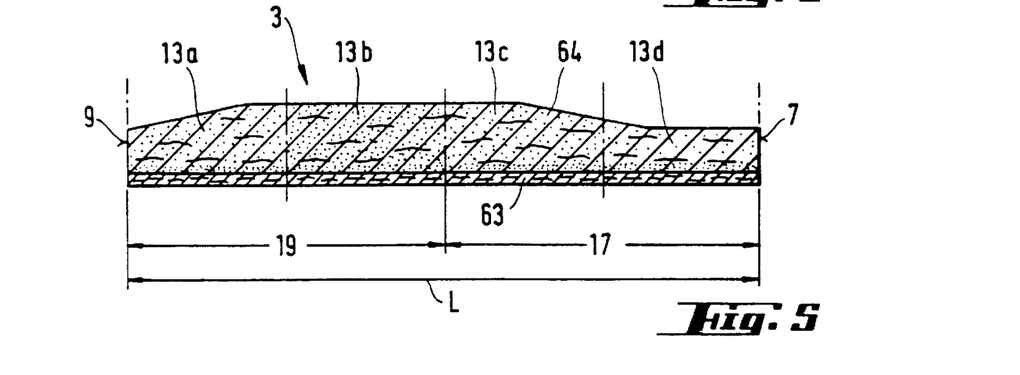

In the embodiment of FIG. 4, the basis weight of the fibrous or foamed absorbent material is equal for the sections 13a–13d in layer 64. The basis weight of the fibrous or foamed absorbent material may typically be about 0.05 g/m$^2$. However, in addition to a varying basis weight of the absorbent gelling material for each section 13a–13d, the basis weight of the fibrous or foamed absorbent material may also vary in each region 13a–13d, as shown in FIG. 5. Again, the core 3 as shown in FIG. 5 can be calendered to a uniform caliper.

Figure 6:
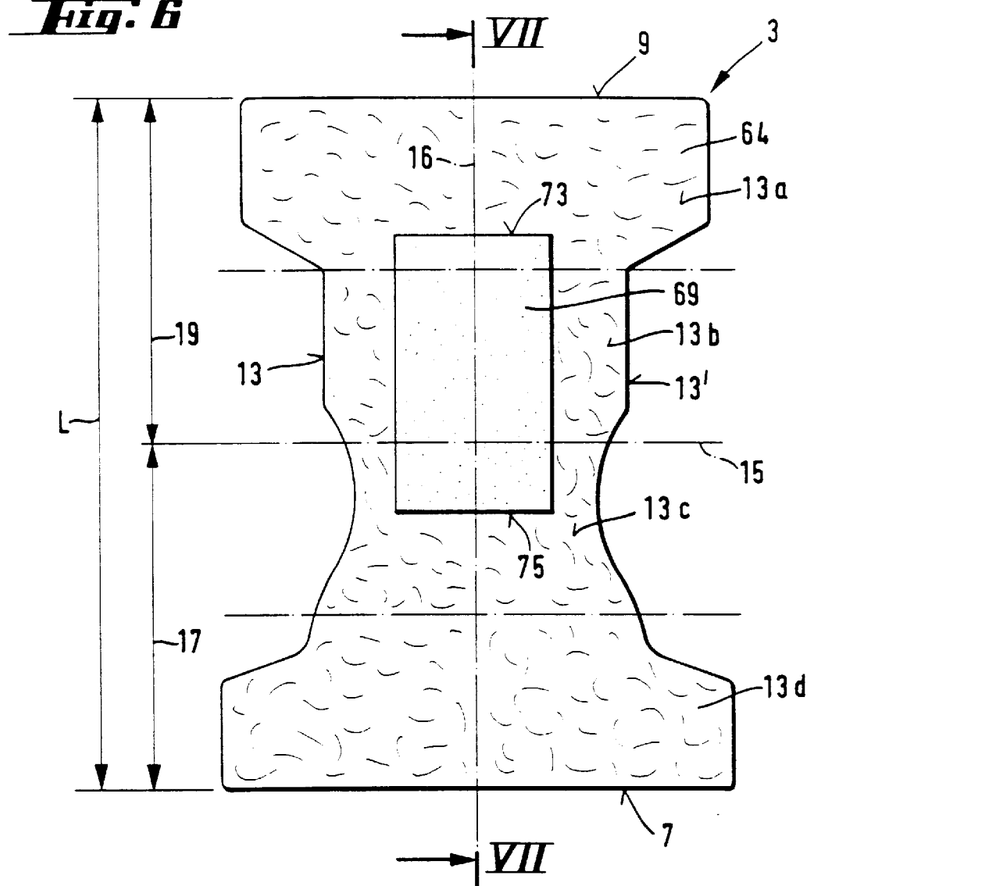
FIG. 6 shows a front elevational view of an absorbent structure comprising an acquisition/distribution layer.

In FIG. 6 a top view of an embodiment of an absorbent core 3 is shown that comprises an acquisition/distribution layer 69, located on top of the layer 64 of core 3. The acquisition/distribution layer serves to quickly collect large gushes of liquids and to isolate these from the body of the wearer until these liquids have been absorbed in the underlying layer 64. The density of the acquisition/distribution layer is preferably between 0.03 and 0.13 g/cm$^3$ the basis weight being between 100 and 500 g/m$^2$, depending on the volume of the gush that is to be taken up. A preferred material for the acquisition/distribution layer 69 is chemically stiffened cellulose material as described in EP-A-0 429 112 (Herron) U.S. Pat. Nos. 4,898,642 (Moore) and 4,889, 597 (Bourbon). Further useful acquisition/distribution layers comprise open networks of thermally bonded synthetic fibers as described in U.S. application Ser. No. 08/141,156 and EP-A-513 148.

An important property of the acquisition/distribution layer 69 is its ability to maintain a sufficient void volume for liquid uptake, even when wet. The fibers in the layer 69 should be sufficiently resilient to not collapse in their wet state upon compression. It was found that layers having a wet compressibility of at least 5 cm$^3$g$^{-1}$ and a drip capacity of at least 10 g g$^{-1}$ can be successfully used in acquisition/distribution layer 69.

The wet compressibility and the drip capacity can be measured by the test described below. All tests are carried out at about 23±2_C. and at 50±10% relative humidity. The specific synthetic urine used in the test methods is commonly known as Jayco SynUrine and is available from Jayco Pharmaceuticals Company of Camp Hill, Pa. The formula for the synthetic urine is: 2.0 g/: of KCl; 2.0 g/l of Na$_2$SO$_4$; 0.85 g/l of (NH$_4$)H$_2$PO$_4$; 0.15 g/l (NH$_4$)H$_2$PO$_4$; 0.19 g/l of CaCl$_2$; ad 0.23 g/l of MgCl$_2$. All of the chemicals are of reagent grade. The pH of the synthetic Urine is in the range of 6.0 to 6.4.

Sample Pad Preparation for Wet Compressibility and Drip Capacity Tests

The sample pads are prepared using a padmaker machine of type such as is described below or an equivalent machine, which provides a consistent and homogeneous laydown of fluff. Four 30 g portions of dry fluff (or equivalent material, for example chemically cross-linked cellulose) are weighed out. A ply of tissue porous enough for air to pass through it while retaining fluff on it, is cut to 36.8 cm×36.8 cm (14.5"×14.5"), and is placed evenly on a forming screen of an air laid felt padmaker machine. The tissue completely covers the forming screen and is made to curve up at its sides to prevent escape of the fluff. The tissue forms the bottom of the pad. The vacuum chamber motor and compressed air supply on the padmaker machine are turned on. One 30 g portion of fluff is added to the sample chamber on the padmaker machine in small amounts via a sample feed and without obstructing the blades of the machine. Compressed air is circulated vigorously in the chamber to expedite separation and passage of the fibres through a plexiglass cylinder and the prismoid column to the forming screen.

The vacuum is turned off and the forming screen is pulled out of the padmaker machine and rotated through a quarter turn in the clockwise direction. The screen is returned to the padmaker machine. Another 30 g portion of fluff is added to the chamber on the machine and the above procedure is repeated. Fluff is added in the same manner until all four portions have been transferred to the forming screen. The forming screen, and the pad formed thereon, is then removed from the padmaker machine, and the pad is carefully transferred from the screen to a piece of cardboard, or similar smooth flat surface. A second ply of tissue is added to the top of the pad, and a second piece of cardboard placed on top of that.

A steel weight having dimensions of around 35.6 cm×35.6 cm×2.5 cm (14"×14"×1") having a weight of around 16.3 kg (36 lbs) is placed on top of the pad for approximately 120 seconds, or longer until the pad is needed. The weight is then removed and the pad is pressed by application of a force of around 4,500 kg (10,000 lbs) on a large Carver press to improve pad integrity. The pad is removed from the press and trimmed on a paper cutter to have dimensions around 30.5 cm×30.5 cm (12"×12"), and is then further cut according to the size required by the particular test in which it is to be used.

The use of a padmaker machine to form the sample pads is not intended to be limiting. Any suitable method can be used provided a consistent and homogeneous laydown of fluff is achieved, which is then compressed under the above conditions to give a pad having substantially the same density and basis weight as achieved above.

Wet Compressibility Test

This test is designed to measure the volume of a pad of fibrous material under varying load conditions when wet. The objective is to measure the fibrous material's resistance to load by measuring the volume maintained under that load.

A fluff test pad is prepared as described above. Any tissue present on the surfaces of the pad is removed. The pad is then densified under a 3.6 kg cm$^{-2}$ (51 psi) load for pad integrity reasons using a Carver laboratory press. The thickness of the pad is measured and its fibre density calculated by pad weight÷(pad thickness×pad area).

The dry weight of the pad is multiplied by 10, and this represents the target wet weight on loading. The dry pad is transferred onto a top loading balance having a 0.01 g sensitivity. Synthetic urine is dispensed slowly onto the pad until the target wet weight is achieved as measured by the balance. The wet pad is carefully transferred onto the surface of a compressibility tester of the Buckeye design, and a weight having substantially the same area as the pad (about 10.2 cm×10.2 cm) and corresponding to a pressure of 77 g cm$^{-2}$ (1.1 psi) is lowered slowly onto the pad. The pad is left for 60 seconds to allow it to equilibrate under the load, and then the thickness of the compressed pad is recorded using calipers. The Wet Compressibility is the void volume per gram of dry fluff and is calculated as follows:

Void Volume (cm$^3$)=Total Volume−Fibre Volume

=(pad thickness under load (cm)×pad area (cm$^2$))−(pad dry weight (g)/fibre density (g cm$^3$)

Wet Compressibility=Void volume per gram=[(pad thickness under load (cm)×pad area (cm$^2$))−(pad dry wt. (g)/fibre density (g cm$^{-3}$)]÷pad dry wt. (g)

where fibre density is calculated from the initial pad weight and thickness measurements (i.e. under no load conditions).

Drip Capacity Test

A sample pad prepared as described above is cut on a paper cutter to have dimensions 7.5 cm×7.5 cm. The pad is weighed and is placed on a large mesh wire screen which is in turn positioned on a drip tray. The whole apparatus is then mounted on a top-loading balance.

Synthetic urine is introduced via a pump (Model 7520-00, as supplied by Cole-Parmer Instruments Company, Chicago, USA) into the centre of the sample pad at a rate of 5±0.25 ml s$^{-1}$. The time for the pad to release the first drop of synthetic urine through the bottom of the pad and into the drip tray is recorded. The pump is immediately stopped as soon as this occurs. The time recorded and the pumping rate are then used to calculate the volume (ml) of synthetic urine absorbed by the sample on reaching saturation, i.e. when the sample starts to drip. The balance can be used to check this periodically, thereby minimising any variation in the pump delivering the synthetic urine. This is known as the Drip Capacity, and is given as the ratio:

{Urine retained by sample pad on saturation (ml)}/{Dry Weight of sample (g)}

Figure 7:
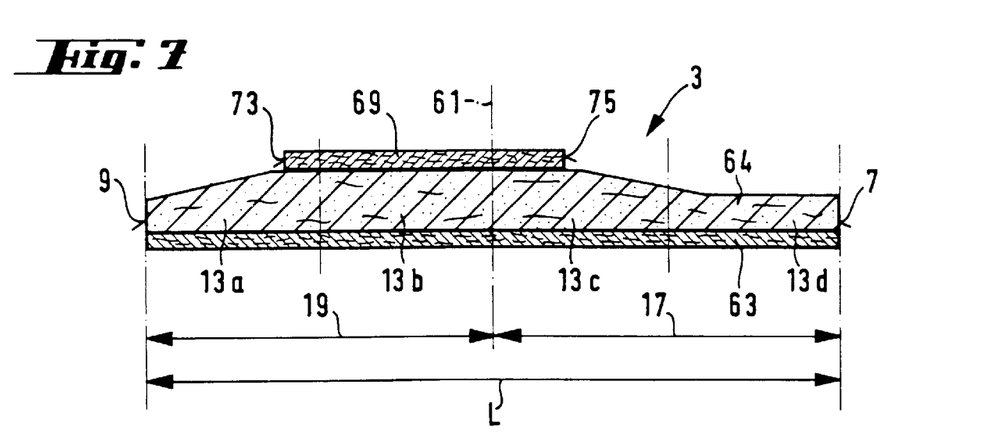
FIG. 7 shows a cross-sectional view of the structure of FIG. 6 along the longitudinal center line.
Figure 8:
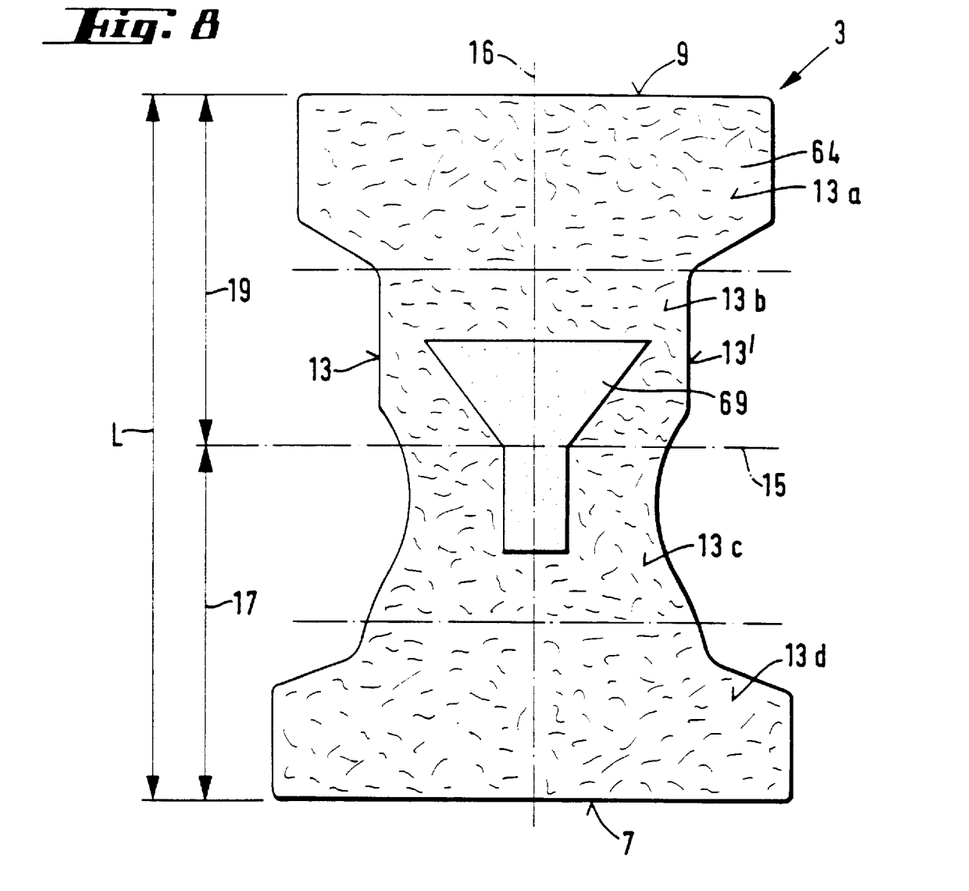
FIG. 8 shows a front elevational view of an absorbent structure having an acquisition/distribution layer.

FIG. 7 shows the cross-sectional view of the core 3 of FIG. 6. In the embodiment of FIGS. 6 and 7, the acquisition/distribution layer 69 is of generally rectangular shape and comprises a back edge 73 and a front edge 75. The distance between the back edge 73 of the acquisition/distribution layer 69 and the cross sectional center line 61 is larger than the distance between the front edge 75 and the cross-sectional center line. For irregularly shaped acquisition/distribution layers 69, as shown in FIG. 8, the surface area of the part of the acquisition/distribution layer 69 located between the transverse center line 15 and the back edge 9 of the core 3 is larger than the surface area of the acquisition/distribution layer 69 located between the transverse center line 15 and the front edge 7 of the core 3. Preferably the ratio of the total weight of absorbent material in the acquisition/distribution layer located in the back half section of the absorbent core 3 and located in the front half section of the acquisition-distribution layer is between 1.1 to 3.

Figure 9:
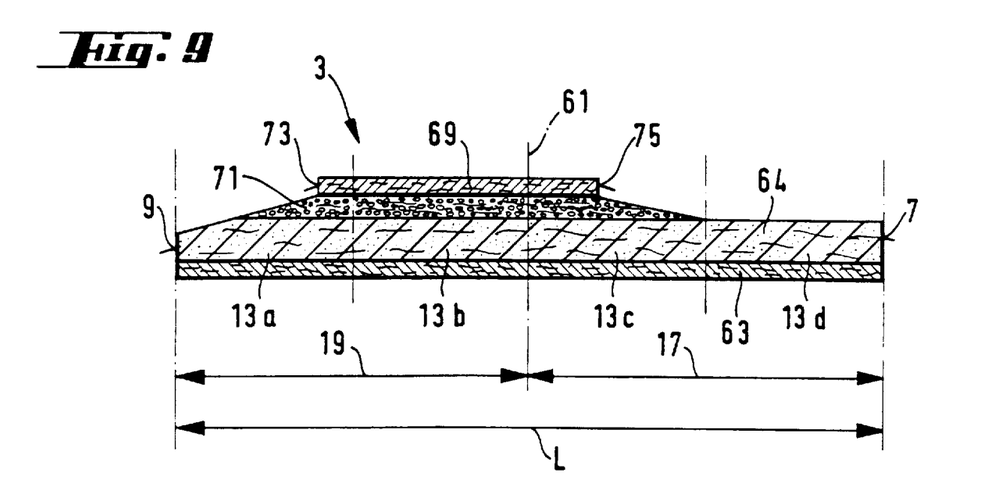
FIG. 9 shows a cross-sectional view of an absorbent structure having a layer of absorbent gelling material located directly underneath the acquisition/distribution layer.

In the embodiment of FIG. 9, an extra layer 71 of absorbent gelling material is located underneath the acquisition/distribution layer 69. This layer of absorbent gelling material serves to quickly drain the layer 69, such that it is ready for subsequent gushes of liquid, and maintains a dry buffer adjacent the skin of the wearer. Absorbent gelling materials of high gel strength as mentioned above are suitable to use in the layer 71, as they maintain a relatively open structure through which liquids can pass to the underlying layer 64 without adverse effects of gel blocking. The absorbent gelling material in layer 71 may be mixed with the fibers in the upper part of the layer 64, and may be introduced in this layer during the airlaying of the fibers of the layer 64, using a powder spray nozzle as described in EP-B-0 330 675.

Alternatively, the layer 71 contains a layer of absorbent gelling material which is not substantially mixed with the fibrous or foamed absorbent material of the layer 64. Such a layer of absorbent gelling material may be bonded to a tissue by means of adhesive or frictional forces, as disclosed in U.S. Pat. No. 4,600,458 (Kramer) or may contain a single layer of loose absorbent gelling material particles. Alternatively, the layer 71 comprises a layer of interparticle-crosslinked particles which form a porous macroscopic aggregate as described in U.S. Pat. Nos. 5,102,597 (Roe) and 5,180,622 (Berg).

When the layers 71 contain a substantially pure layer of absorbent gelling material, it is important that the layer 71 remains permeable for liquids. It was found that absorbent gelling materials having a Gel Layer Permeability of at least $4 \times 10^{-7} cm^3 s/g$ can advantageously be used in the layer 71. The GLP value describes the ability of the absorbent gelling material to maintain a permeable structure and to allow liquid transport through the absorbent gelling material layer, even when wet. The test for measuring the GLP values has been described in detail in European application no. 93309614.1. Alternatively, the absorbent gelling material has an absorption against pressure value (AAP) of at least 23 g/g at a confining pressure of 5 kPa (0.7 psi). A test for measuring the AAP-values has been described in European patent application no. 93909614.1.

For determining the weight of absorbent gelling material in the embodiment of FIG. 9, in the front half and back half sections 17,19 the total weight of absorbent gelling material in each section comprises the absorbent gelling material present in both layers 71 and 64. The regions 13*a* and 13*b* each contain about 20% by weight the absorbent gelling material in the core 3, regions 13*c* and 13*d* each contain 15% by weight and layer 71 contains 30% of the total weight of absorbent gelling material in layers 64 and 71. The absorbent gelling material in the layer 71 need not have the same chemical or physical or physical properties as the absorbent gelling material in the layer 64, but can for instance have a slower absorption speed or a lower absorption under pressure.

Figure 10:
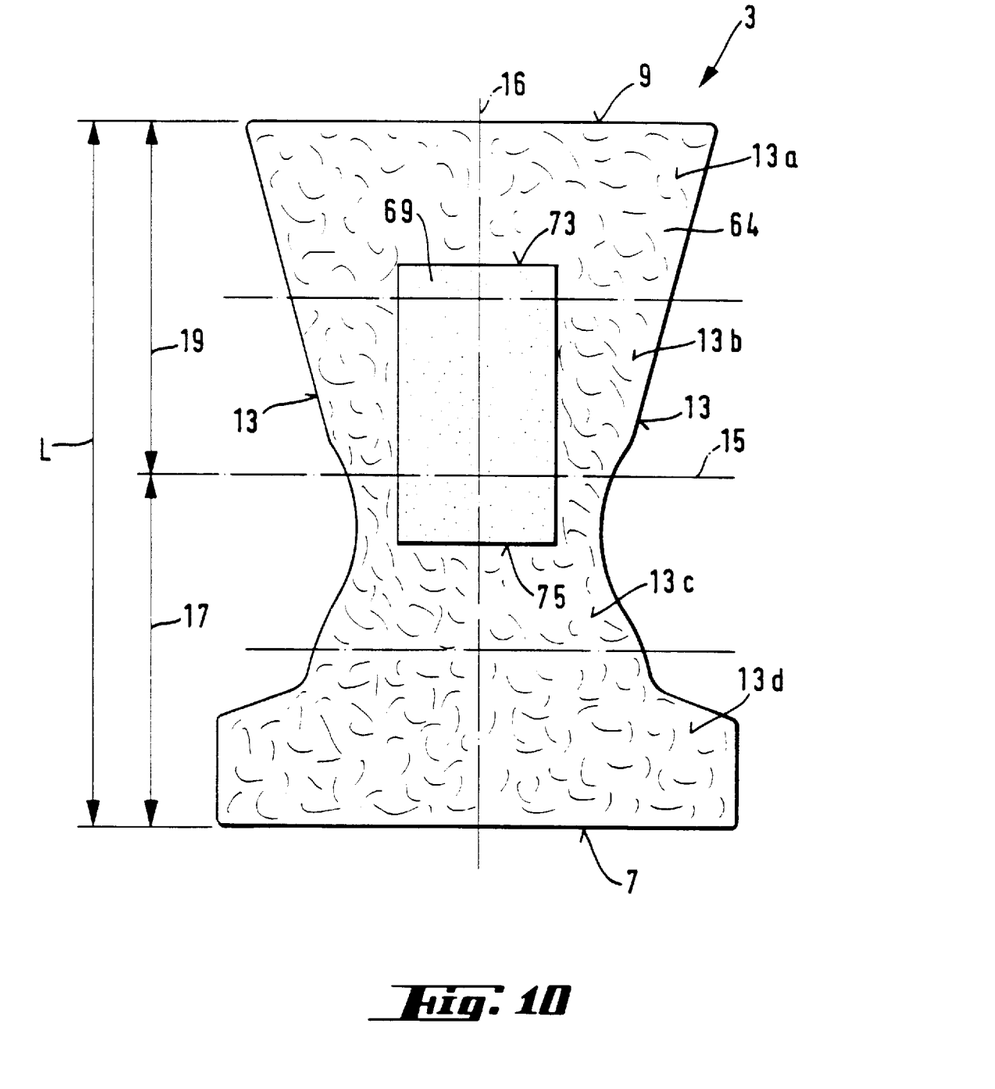
FIG. 10 shows a front elevational view of an absorbent structure having a back half section of relatively large surface area, FIG. 11 schematically shows the region for measuring the average basis capacity of an absorbent structure, and FIG. 12 schematically shows the test equipment for measuring the average basis capacity of an absorbent structure.

In the embodiment of FIG. 10, it is shown that the core 3 has a larger surface area in the back half section of the core 3 to provide an increased absorbent capacity.

In the following example, the rewet properties of a product according to the invention will be determined and will be compared with the rewet properties of similar product which do not have a majority of the absorbent gelling material located in the back half section. The determination of the average basis capacity and the rewet test are set out here below:

Average Basis Capacity

The average basis capacity measures the amounts of liquid absorbed per gram of absorbent material in the central area of the absorbent structure, as indicated in FIG. 11.

First the average basis weight of the material in the central area 6*a*–6*f* is determined in accordance with "Prüfmethode Nr. 1/93 MDS-HI Teil 1; Bestimmung der Flüssigkeitsaufnahme". The absorbent product is laid flat on a surface and the transverse center line 15 that is located midway between the front transverse edge 7 and the back transverse edge 9 and that divides the absorbent core into the front half section 17 and back half section 19, is marked. Likewise the longitudinal center line 16 is marked. A total of up to six test samples 6*a*–6*f* each of 100×100 mm size are labelled and cut out of the absorbent product as detailed in FIG. 11. In case of smaller product size, the number of samples can be reduced. In any case, the samples are taken symetrically around the transverse center line 15.

Typically each sample 6*a*–6*f* will be composed of absorbent material located between and contained by a nonwoven topsheet 24 and a water impervious backsheet 26 or outer material. The samples 6*a*–6*f* are symmetrically removed about the transverse center line above and below the transverse center line. The labelled samples are removed with the aid of a die or laboratory cutter and are weighed with a laboratory balance to an accuracy of 0.05 gram. For each sample the dry weight, $W_i$, is recorded.

Figure 12:
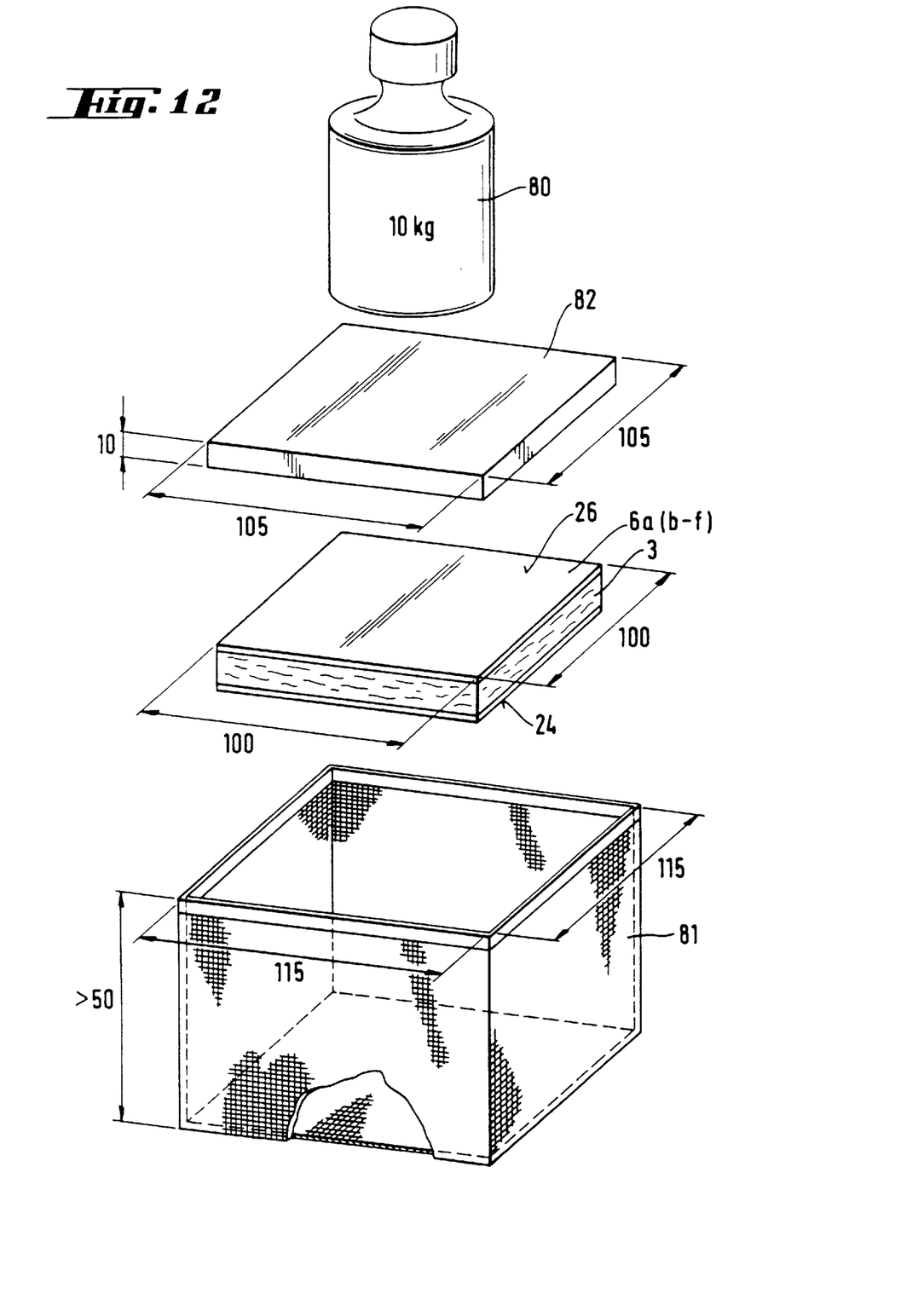

The samples are placed, one at a time, in a metallic meshed basket 81 as illustrated in FIG. 12 with the water impervious backsheet 26 or backing material placed upwards. A perspex plate 82 is placed on top of the sample and the metallic meshed basket 81 is submerged in Jayco synthetic urine which so that the sample and perspex plate 82 are fully submerged for a period of 20 minutes. After 20 minutes, the basket containing the sample is immediately removed and placed on a stand that allows excess test solution to readily drain away. Immediately a 10 kg weight is placed on top of the perspex plate lying on top of the sample 80 for a period of 2 minutes such that a pressure of 100 g/cm² is exerted on the sample. After the 2 minutes the weight and perspex plate are immediately removed and the sample is immediately weighed. The weight of each sample loaded with liquid, $Wl_i$, is recorded.

The average basis capacity (g/g) for the front half section is given by:

$$\frac{1/3}{i} [(W|_i - W_i)/W_i] \text{ [for samples } i = 6d, 6e, 6f)$$

Similarly, the average basis capacity can be determined for the back half section on the basis of samples 6*a*, 6*b* and 6*c*.

Rewet Test

In the rewet test the ability of an absorbent product to retain absorbed liquids inside the core, is measured. In the rewet test, an absorbent diaper is selected, weighed and the elastic components are either cut in half or removed to allow the product to be laid out in its flattened position. Front and back loading points for application of a test solution are clearly marked on the absorbent product. The front loading point is located on the longitudinal center line 16 at a distance 10 cm from the front transverse edge 7 inwards towards the transverse center line 15. The back loading point is located on the longitudinal center line 16 at a distance 15 cm from the back transverse edge 9 inwards towards the transverse center line 15.

In separate tests, either the front or the back loading point is selected and a volume typical of in in-use conditions of 240 ml of Jayco synthetic urine, of chemical composition as described in the text above, is dripped onto the loading point at a rate of 17 ml/sec. A circular weight of 10 Kg and having a diameter of 16 cm and exerting a loading pressure of 50 g/cm² (0.7 psi), is placed onto the center of the loading point for a period of 30 minutes. After 30 minutes the weight is carefully removed and dried and eight (8) layers of pre-weighed filter papers (Eaton Dikeman 631, Nr 5) are immediately placed central onto the loading point and the weight gently lowered, without delay, onto the filter paper for exactly 30 seconds. The weight and filter paper are immediately removed on completion of the 30 seconds and the difference in filter paper weight is recorded as the first rewet value. A second set of eight (8) layers of pre-weighed filter papers are immediately placed central onto the loading point and the weight gently lowered, without delay, onto the filter paper for exactly 30 seconds. The weight and filter paper are immediately removed on completion of the 30 seconds and the difference in filter paper weight is recorded as the second rewet value. The total rewet is the sum of the two individual rewet values, i.e. rewet=1 st+2 nd rewet values.

Comparative Example

In this example three incontinence briefs, or diapers, were wetted in the front and back half sections and the rewet values were measured in each section. The average basis capacity of the back half section and the front half section of each sample was determined by the method described above. The samples are similar in terms of their dimensions and capacity and are representative of absorbent products typically in use for adult heavy incontinence sufferers. The following three products are compared:

1) An incontinence brief having an absorbent core according to the invention, for the user size group 'Medium'.
2) A incontinence brief otherwise identical to 1) but with a absorbent core comprising more absorbent gelling material in the front half section than in the back half section, and
3) A commercially available incontinence brief sold under the trade name Tena Slip Super (Art. No. 711200, manufacturer Mölnlycke AB) in the user size group 'Medium'.

Results of the rewet testing and absorbent capacity measurements of the above products are given in Table I below.

From Table I it can be seen that for sample 1, which has in the back half section a larger amount of absorbent gelling material and a higher average basis capacity, the rewet in the back half section is smaller by about a factor 10 compared to the rewet of samples 2 and 3. Because of the low rewet values in the back half section, the samples 1 are especially adapted for use by bedridden users. In the lying down position, the liquid will be stored predominantly in the back half section of the core. Maintaining the rewet at the lowest possible level is especially important with bedridden users to avoid a negative impact on the skin of wetness and pressures which normally occur with incontinent bedridden users.

TABLE I

Comparison of the average basis capacity and rewet values in the front half section and back half section for three adult incontinence products.

| Parameter | Sample 1 Absorbent gelling material predominately in back half section | Sample 2 Absorbent gelling material predominately in front half section | Sample 3 Commercially available product |
|---|---|---|---|
| Product Dimensions | | | |
| Product Length (mm) | 838 | 838 | 805 |
| Product Width front (mm) | 625 | 625 | 650 |
| Product Width back (mm) | 637 | 637 | 634 |
| Absorbent Structure | | | |
| Core Length (mm) | 651 | 651 | 636 |
| Core width Centre (15) (mm) | 200 | 200 | 175 |
| Core Width Back (9) (mm) | 325 | 325 | 330 |
| Core Width Front (7) (mm) | 325 | 325 | 325 |
| Total Core Area (sqcm) | 1597 | 1597 | 1580 (±60) |
| Total Core Weight (g) | 103 | 103 | 110 (±5) |
| Front Half Section Airfelt/Fibrous Material | | | |
| Area (sqcm) | 764 | 764 | 754 (±50) |
| Weight (g) | 43.5 | 43.5 | 46 |

TABLE I-continued

Comparison of the average basis capacity and rewet values in the front half section and back half section for three adult incontinence products.

| Parameter | Sample 1 Absorbent gelling material predominately in back half section | Sample 2 Absorbent gelling material predominately in front half section | Sample 3 Commercially available product |
|---|---|---|---|
| Basis Weigh (g/sqcm) | 0.056 | 0.056 | 0.062 (±3) |
| Absorbent Gel Material | | | |
| Area (sqcm) | 495 | 495 | 754 |
| Weight (g) | 4.5 | 7.5 | 6 (±0.5) |
| Basis Weight (g/sqcm) | 0.0091 | 0.015 | 0.008 |
| Test Results Front Half | | | |
| Average Basis Capacity (g/g) | 9.2 | 10.9 | 8.6 |
| Rewet (g) | 1.6 | 0.19 | 2.7 |
| Back Half Section Airfelt/Fibrous Material | | | |
| Area (sqcm) | 833 | 833 | 826 |
| Weight (g) | 47.5 | 47.5 | 51 (±3) |
| Basis Weigh (g/sqcm) | 0.056 | 0.056 | 0.062 |
| Absorbent Gel Material | | | |
| Area (sqcm) | 495 | 495 | 826 |
| Weight (g) | 7.5 | 4.5 | 6 (±0.5) |
| Basis Weight (g/sqcm) | 0.015 | 0.091 | 0.0073 |
| Test Results Back Half | | | |
| Average Basis Capacity (g/g) | 10.9 | 9.2 | 8.6 |
| Rewet (g) | 0.17 | 1.6 | 2.8 |

What is claimed is:

1. An absorbent structure comprising:
    at least one layer of fibrous or foamed absorbent material,
    a front transverse edge, a back transverse edge and two longitudinal sides,
    a transverse center line located midway between said front transverse edge and said back transverse edge,
    a front half section located between said transverse center line and said front transverse edge,
    a back half section located between said transverse center line and said back transverse edge, and
    absorbent gelling material having an Absorption Against Pressure of at least 23 g/g under a confining pressure of 5 kPa,
    wherein more than half the weight of said absorbent gelling material is disposed in said back half section of said absorbent structure.

2. The absorbent structure of claim 1 further comprising an acquisition/distribution layer having a surface overlying said layer of absorbent material, wherein more than half of said surface of said acquisition/distribution layer is disposed in said back half section of said absorbent structure.

3. The absorbent structure of claim 2, wherein said acquisition/distribution layer has a wet compressibility of at least 5 cm³/g and a drip capacity of at least 10 g/g.

4. The absorbent structure of claim 2, wherein said acquisition/distribution layer comprises chemically stiffened cellulosic fibers.

5. The absorbent structure of claim 2, wherein said acquisition/distribution layer comprises synthetic thermally bonded fibers.

6. The absorbent structure of claim 2, wherein absorbent gelling material is located underneath and adjacent to said acquisition/distribution layer.

7. The absorbent structure of claim 6, wherein the basis weight of said absorbent gelling material located underneath and adjacent to said acquisition/distribution layer is between 50 and 400 $g/m^2$.

8. The absorbent structure of claim 1, wherein said absorbent gelling material has a Gel Layer Permeability value of at least $4 \times 10^{-7} cm^3/s/g$.

9. The absorbent structure of claim 1, further comprising a longitudinal center line, wherein the distance between a longitudinal side and said longitudinal center line substantially monotonically increases from said transverse center line to said back transverse edge.

10. An absorbent structure comprising:

at least one layer of fibrous or foamed absorbent material, a front transverse edge, a back transverse edge and two longitudinal sides, a transverse center line located midway between said front transverse edge and said back transverse edge, a front half section located between said transverse center line and said front transverse edge, a back half section located between said transverse center line and said back transverse edge, and absorbent gelling material having a Gel Layer Permeability value of at least $4 \times 10^{-7} cm^3/s/g$, wherein more than half the weight of said absorbent gelling material is disposed in said back half section of said absorbent structure.

11. The absorbent structure of claim 10 further comprising an acquisition/distribution layer having a surface overlying said layer of absorbent material, wherein more than half of said surface of said acquisition/distribution layer is disposed in said back half section of said absorbent structure.

12. The absorbent structure of claim 11, wherein said acquisition/distribution layer comprises chemically stiffened cellulosic fibers.

13. The absorbent structure of claim 11, wherein said acquisition/distribution layer comprises synthetic thermally bonded fibers.

14. The absorbent structure of claim 11, wherein absorbent gelling material is located underneath and adjacent to said acquisition/distribution layer.

15. The absorbent structure of claim 14, wherein the basis weight of said absorbent gelling material located underneath and adjacent to said acquisition/distribution layer is between 50 and 400 $g/m^2$.

16. The absorbent structure of claim 10 further comprising a longitudinal center line, wherein the distance between a longitudinal side and said longitudinal center line substantially monotonically increases from said transverse center line to said back transverse edge.

17. An absorbent structure comprising:

at least one layer of fibrous or foamed absorbent material, a front transverse edge, a back transverse edge and two longitudinal sides, a transverse center line located midway between said front transverse edge and said back transverse edge, a front half section located between said transverse center line and said front transverse edge, a back half section located between said transverse center line and said back transverse edge, absorbent gelling material, and an acquisition/distribution layer having a surface overlying said layer of absorbent material, said acquisition/distribution layer further having a wet compressibility of at least 5 $cm^3/g$ and a drip capacity of at least 10 g/g, wherein more than half the weight of said absorbent gelling material and more than half of said surface of said acquisition/distribution layer are disposed in said back half section of said absorbent structure.

18. The absorbent structure of claim 17, wherein said acquisition/distribution layer comprises chemically stiffened cellulosic fibers.

19. The absorbent structure of claim 17, wherein said acquisition/distribution layer comprises synthetic thermally bonded fibers.

20. The absorbent structure of claim 17 wherein said acquisition/distribution layer has a longitudinal center line, a back edge and two longitudinal sides, and the distance between said longitudinal center line and each said longitudinal side of said acquisition/distribution layer increases from said transverse center line to said back edge.

21. The absorbent structure of claim 17, wherein absorbent gelling material is located underneath and adjacent to said acquisition/distribution layer.

22. The absorbent structure of claim 21, wherein the basis weight of said absorbent gelling material located underneath and adjacent to said acquisition/distribution layer is between 50 and 400 $g/m^2$.

23. The absorbent structure of claim 17 further comprising a longitudinal center line, wherein the distance between a longitudinal side and said longitudinal center line substantially monotonically increases from said transverse center line to said back transverse edge.

24. An absorbent structure having an absorbent material layer, said layer comprising:

fibrous or foamed absorbent material, absorbent gelling material, a front transverse edge, a back transverse edge, and two longitudinal sides, a transverse center line located midway between said front transverse edge and said back transverse edge, a front half section extending between said transverse center line and said front transverse edge having a caliper, and a back half section extending between said transverse center line and said back transverse edge having a caliper which is higher than said caliper of said front half section, wherein more than half the weight of said absorbent gelling material is disposed in said back half section of said absorbent material layer;

said absorbent structure further comprising an acquisition/distribution layer having a surface overlying said absorbent material layer, wherein more than half of said surface of said acquisition/distribution layer overlies said back half section of said absorbent material layer.

* * * * *